(12) United States Patent
Shields

(10) Patent No.: US 9,005,137 B2
(45) Date of Patent: Apr. 14, 2015

(54) DEVICE FOR COLLECTING A URINE SAMPLE

(75) Inventor: Janice M. Shields, San Marcos, CA (US)

(73) Assignee: Angele Innovations, LLC, San Marcos, CA (US)

( * ) Notice: Subject to any disclaimer, the term of this patent is extended or adjusted under 35 U.S.C. 154(b) by 1015 days.

(21) Appl. No.: 13/100,818

(22) Filed: May 4, 2011

(65) Prior Publication Data

US 2012/0283597 A1 Nov. 8, 2012

(51) Int. Cl.
*A61B 5/00* (2006.01)
*B65D 81/00* (2006.01)
*B65D 33/00* (2006.01)
*A61B 5/20* (2006.01)
*A61B 10/00* (2006.01)
*A61F 5/451* (2006.01)

(52) U.S. Cl.
CPC ............... *A61B 5/207* (2013.01); *A61B 10/007* (2013.01); *A61F 5/451* (2013.01); *A61B 2503/04* (2013.01)

(58) Field of Classification Search
CPC ............... A61B 5/207; A61B 2503/04; A61B 10/00045; A61B 10/007; A61F 5/451
USPC .................................................. 600/572–584
See application file for complete search history.

(56) References Cited

U.S. PATENT DOCUMENTS

| | | | |
|---|---|---|---|
| 5,100,619 A * | 3/1992 | Baker et al. | 422/408 |
| 6,197,011 B1 * | 3/2001 | Freitas et al. | 604/385.03 |
| 2004/0071594 A1 * | 4/2004 | Malone et al. | 422/58 |
| 2008/0274014 A1 * | 11/2008 | Jumonville et al. | 422/57 |

OTHER PUBLICATIONS

Department of Biomedical Engineering, University of Wisconsin-Madison, Premature Infant Urine Collection Device, Preliminary Design Report BME Design 201, Mar. 15, 2002.
T. L. Pokorski, B. E. Ortel, J. L. Saxton, D. G. Erickson, Aviators' Urine Collection Devices: Preliminary Laboratory Trials, NAMRL Special Report 96-1, Jan. 9, 1996, Naval Aerospace Medical Research Laboratory.
Wikipedia article, Urine Collection Device, Wikipedia Free Encyclopedia, Oct. 14, 2011, (at website http://en.wikipedia.org/wiki/urine_collection_device).

* cited by examiner

*Primary Examiner* — Rene Towa
(74) *Attorney, Agent, or Firm* — Nydegger & Associates

(57) ABSTRACT

A device and method for collecting a urine sample from a neonate is provided. The device is attached to the neonate shortly after birth and removed after the neonate produces a urine sample. An interior shell and an exterior shell form the device, and an absorbent material is located inside the interior shell to absorb the urine sample. The interior shell and the exterior shell are connected by a hinge and are initially in a nesting position, with the exterior shell on top of the interior shell. After the urine sample is absorbed by the absorbent material, the exterior shell is rotated around an axis defined by the hinge to contact and compress the absorbent material to release the urine sample for collection.

19 Claims, 2 Drawing Sheets

DEVICE FOR COLLECTING A URINE SAMPLE

FIELD OF THE INVENTION

The present invention pertains generally to systems and methods for collecting urine samples. More particularly, the present invention pertains to a device for collecting a urine sample from a patient without requiring active participation by the patient. The present invention is particularly, but not exclusively, useful as a system and method for collecting a urine sample from a neonate immediately after birth.

BACKGROUND OF THE INVENTION

Prior to the birth of a baby, medical personnel conduct various examinations and tests on the baby and its mother in order to anticipate any medical issues which require treatment after birth. In doing this, medical staff can develop an appropriate course of care for the baby after birth. In some instances this course of care may require procedures to begin immediately at the birth of the baby. In addition to physical examinations, medical staff will also want to know about any behavior of the mother during pregnancy that may have adversely impacted the health, growth, or development of the baby. Specifically, the use of alcohol and drugs are of utmost interest to medical personnel.

Using current medical technology, many medical issues can be diagnosed prior to the birth of a baby. But, a baby may have medical problems that were not apparent or diagnosable while the baby was still in utero. And, if a mother has not been receiving any type of pre-natal care, there likely was not enough time to conduct examinations and tests prior to the birth of the baby. Without appropriate pre-natal care, medical personnel will have to rely solely on the mother for information regarding her pregnancy. In many cases, however, a mother may not be truthful with medical personnel if she engaged in questionable behavior that may have caused medical problems for her child. Further, neonates are also frequently screened for urinary tract infections.

One common method of medical diagnosis is urinalysis. In most cases, a urine sample is easily obtained as the process is relatively simple and does not require any type of assistance from another person. But, in the case of a neonate, the process is more difficult as a neonate has no control over its urinary functions. Moreover, a neonate cannot collect a urine sample the way a child or an adult can. It will be appreciated that these same issues may also pertain to comatose adults, and nursing home patients. However, under certain circumstances, even older patients may be unable to assist in collecting a urine sample.

In light of the above, it is an object of the present invention to provide a device for collecting a urine sample from a neonate. Another object of the present invention is to provide a device for collecting a urine sample from a neonate immediately after birth. Another object of the present invention is to provide a device for collecting a urine sample from a neonate that is easy to use, is relatively simple to manufacture, and is comparatively cost effective.

SUMMARY OF THE INVENTION

In accordance with the present invention, a device and method for obtaining a urine sample from a neonate are provided. The intent is to obtain a urine sample from a neonate who cannot actively participate in the collection process. To do this, a device requires placing an absorbent material over the genitalia of a neonate to collect the urine sample.

Structurally, an interior shell is provided to house the absorbent material and to securely hold the absorbent material against the neonate during collection of the urine sample. Connected to the interior shell is an exterior shell that can be rotated relative to the interior shell from a nesting position, where it is positioned on top of the interior shell, to a dispensing position, where it contacts the absorbent material. Specifically, when the exterior shell is rotated into contact with the absorbent material, the absorbent material can then be compressed between the exterior shell and the interior shell to eject the urine sample from the device for collection and medical analysis.

The device of the present invention is characterized by an absorbent material along with an interior shell and an exterior shell. Both the interior shell and the exterior shell have respective inner (concave) and outer (convex) surfaces. Furthermore, the interior shell is formed with a hollow, which is a space or cavity formed by the concave shape of the interior shell. It should be noted that the exterior shell has the same concave/convex shape as the interior shell. As envisioned for the present invention, the absorbent material is positioned inside the hollow and held against the inner surface of the interior shell. To hold the absorbent material against the inner surface of the interior shell, a variety of connection methods can be used. For example, the absorbent material may be glued or taped to the inner surface or it may be temporarily held against the inner surface using a hook and loop-type fastener. Regardless what type of connection means is used, the absorbent material must remain sterile to protect the integrity of the urine sample and to protect the health of the patient. In a preferred embodiment, the absorbent material is a sponge, but other types of absorbent materials may also be used. Additionally, the absorbent material and shell may be formed with a groove to receive and accommodate the male genitalia.

As stated previously, the interior shell has an inner (concave) surface and an outer (convex) surface. Likewise, the exterior shell also has an inner (concave) surface and an outer (convex) surface. The interior shell and the exterior shell will both be the same and will be either oval-shaped or circular-shaped. In a preferred embodiment, the interior shell is constructed with a lip surrounding the periphery of the interior shell. This lip is coated with an adhesive material to secure the device to the neonate, and the adhesive material will be exposed by peeling off any protective tape that covers the lip before use. In an alternate embodiment, adhesive strips can be attached to the device for securing the device to the neonate. Additionally, the interior shell and the exterior shell are joined by a hinge. In detail, the hinge is a living hinge that defines an axis around which the exterior shell can be rotated. A tab is optionally provided on the exterior shell to disengage the exterior shell from the interior shell to move the exterior shell from the nesting position to the dispensing position. The tab, the living hinge, the interior shell, and the exterior shell are all made of semi-rigid plastic. And, as envisioned for the present invention, the semi-rigid plastic will be clear, but colored plastic can also be used. For instance, a blue plastic device may be produced for male neonates, and a pink plastic device may be produced for female neonates.

In operation, the device is removed from its protective packaging that is intended to ensure the device remains sterile prior to use. If the adhesive lip is used, tape covering the adhesive lip is removed. Once the adhesive lip is exposed, the device is positioned against the genitalia of the neonate by placing the lip of the device against the neonate and lightly pressing it against the neonate. If the alternate embodiment with the adhesive strips is used, the device is secured by placing a portion of each adhesive strip on the device and on the neonate. Both methods of securing the device to the neonate are intended to allow the device to remain in place for several hours if required.

When the neonate urinates into the device, the urine is absorbed by the absorbent material. At this point, the device is removed from the neonate. After removal, the tab of the exterior shell is lifted to disengage the exterior shell from the interior shell. Further, the tab is then used to rotate the exterior shell from the nesting position to the dispensing position. Once the exterior shell reaches the dispensing position, the device can be rotated by hand to an angle of approximately 45 degrees so the tab of the exterior shell is facing the ground. The absorbent material can then be compressed between the exterior shell and the interior shell to squeeze (pressure) urine from the absorbent material and into a sterile cup. By rotating the device in this manner, the urine sample flows out of the exterior shell in only one direction away from the hinge. Pressure continues to be exerted on the exterior shell until enough urine is collected to produce a sample suitable for analysis.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENTS

Figure 1:
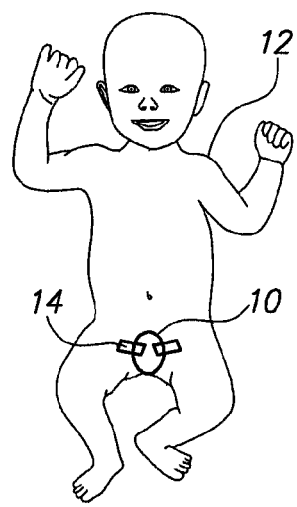
FIG. 1 is a top plan view of the present invention as it is being used in its intended environment.

Referring initially to FIG. 1, the device 10, in accordance the present invention, is shown in its operational environment positioned on the genitalia of a neonate 12. As can be seen in FIG. 1, for one embodiment of the present invention, the device 10 may be held against the neonate 12 by adhesive strips 14 that are secured to both the device 10 and the neonate 12.

Figure 2:
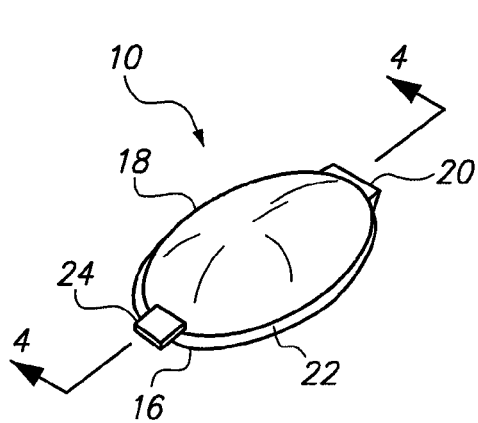
FIG. 2 is a top perspective view of the present invention showing the invention in its initial configuration.

Referring now to FIG. 2, the device 10 is shown in its initial configuration prior to placement against the genitalia of the neonate 12. As shown, the device 10 comprises an interior shell 16 and an exterior shell 18 connected by a hinge 20. In a preferred embodiment as shown in FIG. 2, the only part of the interior shell 16 visible in FIG. 2 is a rounded lip 22 formed around the periphery of the interior shell 16. This lip 22 will be covered with an adhesive material to secure the device 10 to the neonate 12 with or without the use of the adhesive strips 14 (shown in FIG. 1). In FIG. 2, the exterior shell 18 is in a nesting position where the exterior shell 18 is on top of, or covering, the interior shell 16. FIG. 2 also shows the exterior shell 18 is constructed with a tab 24 that is used to disengage the exterior shell 18 from the interior shell 16 when the exterior shell 18 is moved from the nesting position.

Figure 3:
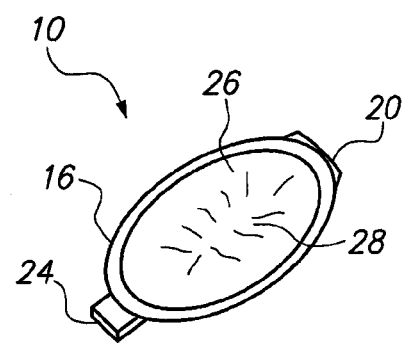
FIG. 3 is a perspective view of the present invention as shown in FIG. 2 with the invention still in its initial configuration, and turned upside down.

Now referring to FIG. 3, the underside of the device 10 is shown. In this view, an absorbent material 26 can be seen inside the interior shell 16. Preferably, the absorbent material is white in color so waste from the neonate 12 can be seen, and the absorbent material is of a type that is well known in the pertinent art. Also, a groove 28 formed in the absorbent material 26 is shown. In a modification of the device 10, it may be desirable to also have the shells 16 and 18 formed with an extension of the groove 28 to accommodate certain patients. The hinge 20 and the tab 24 are also visible in FIG. 3.

Figure 4A:
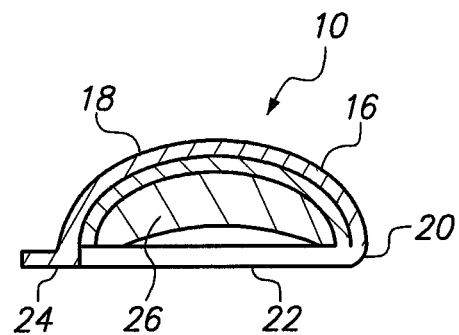
FIG. 4A is a cross-sectional view of the present invention as would be seen along the line 4-4 in FIG. 2, with the invention in its initial configuration.

In FIG. 4A, the device 10 is shown in its initial configuration along line 4-4 in FIG. 2. In this configuration, the device 10 is in a first configuration referred to as a nesting position. In the nesting position, the exterior shell 18 covers the interior shell 16. The nesting position is used to collect the urine sample from the neonate 12 or other patient. When the device 10 is in the nesting position, the device 10 is attached to the neonate 12 by gently pressing the lip 22 of the interior shell 16 around the genitalia of the neonate 12. As disclosed previously, the rounded lip 22 is covered with adhesive material to hold the device 10 around the genitalia of the neonate 12.

Figure 4B:
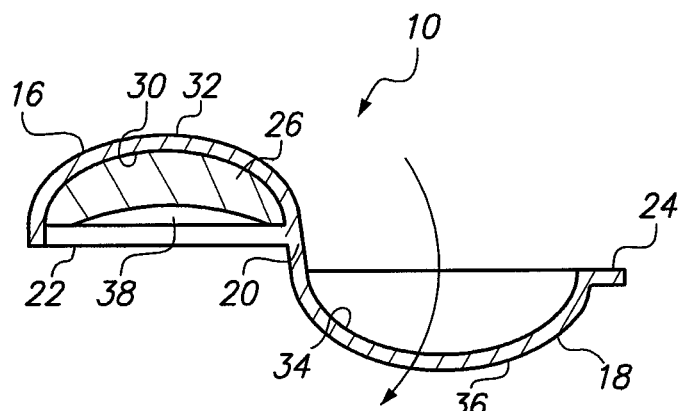
FIG. 4B is a cross-sectional view of the present invention as would be seen along the line 4-4 in FIG. 2, with the invention in an intermediate configuration during transition between its initial configuration and a final configuration.

In FIG. 4B, a view of the device 10 of the present invention is shown along line 4-4 in FIG. 2. This view shows the device 10 after the urine sample has been collected and the device 10 has been removed from the neonate 12. Once the device 10 is removed from the neonate 12, the exterior shell 18 is disengaged from the interior shell 16 and is rotated into a dispensing position where the exterior shell 18 forces the urine sample out of the absorbent material 26. In this view, further details of the interior shell 16 and the exterior shell 18 are apparent. Specifically, an inner concave surface 30 and an outer convex surface 32 of the interior shell 16 and an inner concave surface 34 and an outer convex surface 36 of the exterior shell 18 are shown. In addition, a hollow 38 is shown in the interior shell 16. In detail, the hollow 38 is an interior cavity formed by the concave shape of the interior shell 16. As shown, the absorbent material 26 is held against the inner surface 30 of the interior shell 16, and the absorbent material 26 occupies a position within the hollow 38.

Figure 4C:
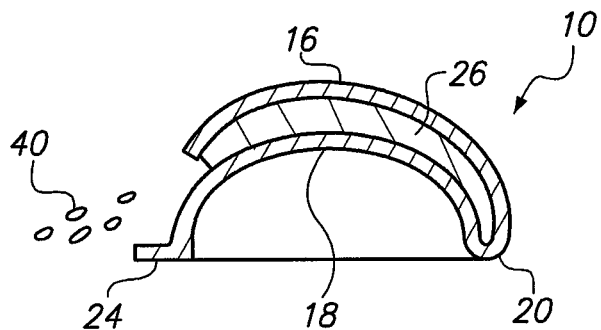
FIG. 4C is a cross-sectional view along the line 4-4 of the present invention as seen in FIG. 2 with the invention in its final configuration.

Now referring to FIG. 4C, the device 10 of the present invention is shown along line 4-4 in FIG. 2 in the dispensing position where the urine sample is collected for analysis. As shown, the exterior shell 18 is shown exerting pressure against the interior shell 16 with the absorbent material 26 therebetween. Further, FIG. 4C illustrates the urine sample 40 being ejected from the absorbent material 26.

Cross-referencing FIG. 4B with FIG. 4C, an operation of the device 10 of the present invention is illustrated. As shown in FIG. 4B, the device 10 is shown as the exterior shell 18 is moved from the nesting position to the dispensing position. To begin rotating the exterior shell 18, the tab 24 is lifted to disengage the exterior shell 18 from the interior shell 16 and move the exterior shell 18 to the dispensing position. The exterior shell 18 is rotated about an axis defined by the hinge 20 until it makes contact with the absorbent material 26 as depicted in FIG. 4C. By using the hinge 20, the exterior shell 18 rotates along a predicted path from the nesting position to the dispensing position. Once contact is made between the exterior shell 18 and the absorbent material 26, the exterior shell 18 is pressed against the interior shell 16 with the absorbent material 26 between the two shells. This action will eject the urine sample 40 from the absorbent material 26. Pressure continues to be exerted by the exterior shell 18 until a sufficient amount of the urine sample 40 is collected. Once the urine sample 40 has been collected, the device 10 is discarded.

While the particular Device for Collecting a Urine Sample as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A device for attachment to a neonate to collect a urine sample, comprising:
    an interior shell having a concave inner surface and a convex outer surface, where the concave inner surface forms a hollow;
    an absorbent material held in the hollow against the inner surface of the interior shell for absorbing the urine sample while the device is attached to the neonate with the absorbent material positioned against the genitalia of the neonate; and
    an exterior shell connected to the interior shell by a hinge, wherein the exterior shell has a concave inner surface and a convex outer surface, and wherein the exterior shell is movable via the hinge from a nesting position to a dispensing position, wherein in the nesting position the inner surface of the exterior shell is in contact with the outer surface of the interior shell to expose the absorbent material during attachment of the device to the neonate, and in the dispensing position the outer surface of the exterior shell contacts and compresses the absorbent material against the interior shell to release the urine sample from the absorbent material and dispense the urine sample from the device;
    wherein said device further includes at least one adhesive strip having a first end for connecting the strip to the neonate and a second end attached to an outer surface of the device, to hold and position the device against the genitalia of the neonate.

2. A device as recited in claim 1 wherein the interior shell is formed with a lip around the periphery of the interior shell, and wherein the lip is coated with an adhesive material for holding the device against the genitalia of the neonate.

3. A device as recited in claim 1 wherein the interior shell and the exterior shell are made of clear, semi-rigid plastic.

4. A device as recited in claim 1 wherein the device is discarded after the urine sample is released from the absorbent material.

5. A device as recited in claim 1 wherein the interior shell and the exterior shell are oval-shaped.

6. A device as recited in claim 1 wherein the interior shell and the exterior shell are circular-shaped.

7. A device as recited in claim 1 wherein the hinge is a living hinge defining an axis and is constructed of semi-rigid plastic, wherein the living hinge allows for rotation about the axis to move the exterior shell between the nesting position and the dispensing position.

8. A device as recited in claim 1 further comprising a tab connected to the exterior shell, wherein the tab is lifted to disengage the exterior shell from the interior shell in order to move the exterior shell from the nesting position to the dispensing position.

9. A device as recited in claim 1 wherein the absorbent material is formed with a groove for receiving male genitalia.

10. A method for collecting a urine sample from a neonate which comprises the steps of:
    providing a device for collecting the urine sample, wherein the device has an interior shell having an inner surface forming a hollow and an outer surface, and wherein the device has an exterior shell having an inner surface and an outer surface and the exterior shell is connected to the interior shell by a hinge, and further wherein an absorbent material is held in the hollow against the inner surface of the interior shell for absorbing the urine sample;
    attaching the device against the genitalia of the neonate in a nesting position wherein the inner surface of the exterior shell is in contact with the outer surface of the interior shell to expose the absorbent material;
    collecting the urine sample with the device;
    removing the device from the genitalia of the neonate after collecting the urine sample;
    rotating the exterior shell via the hinge from the nesting position to a dispensing position wherein the outer surface of the exterior shell contacts the absorbent material; and
    pressing the exterior shell against the interior shell to compress the absorbent material therebetween to eject the urine sample from the absorbent material and dispense the urine sample from the device.

11. A method as recited in claim 10 wherein the interior shell is formed with a lip around the periphery of the interior shell, wherein the lip is coated with an adhesive material for accomplishing the attaching step.

12. A method as recited in claim 10 wherein the hinge of the rotating step is a living hinge defining an axis and is made of semi-rigid plastic, wherein the living hinge allows for rotation between the nesting position and the dispensing position about the axis.

13. A method as recited in claim 10 further comprising the step of discarding the device after the urine sample is released from the absorbent material.

14. A method as recited in claim 10 wherein the interior shell and the exterior shell are oval-shaped.

15. A device for attachment to a neonate to collect a fluid sample comprising:
    an absorbent material for absorbing the fluid sample;
    a first member formed with a hollow for housing the absorbent material; and
    a second member connected to the first member by a hinge, wherein the first member is nested into the second member, wherein the hinge guides the second member along a predictable rotational path for changing the device from a first configuration wherein the second member is on top of the first member for attaching the device to the neonate to a second configuration wherein the second member is beneath the first member with the absorbent material therebetween for dispensing the fluid sample from the device;
    wherein said device further includes at least one adhesive strip having a first end for connecting the strip to the neonate and a second end attached to an outer surface of the device, to hold and position the device against the genitalia of the neonate.

16. A device as recited in claim 15 wherein the first member is formed with a lip around the periphery of the first member, and wherein the lip is coated with an adhesive material for holding the device against the neonate.

17. A device as recited in claim 15 wherein the fluid is ejected from the absorbent material when the second member is in the second configuration.

18. A device as recited in claim 15 wherein the hinge is a living hinge.

19. A device as recited in claim 17 wherein the device is discarded after the fluid sample is ejected from the absorbent material.

\* \* \* \* \*